US012778888B2

(12) United States Patent
Sadabad et al.

(10) Patent No.: US 12,778,888 B2
(45) Date of Patent: Nov. 3, 2026

(54) METHOD AND SYSTEM FOR OTOTOPICAL DELIVERY USING NANOPARTICLES FOR EAR INFECTION DIAGNOSIS AND TREATMENT

(71) Applicant: THE BOARD OF TRUSTEES OF THE LELAND STANFORD JUNIOR UNIVERSITY, Stanford, CA (US)

(72) Inventors: Raana Kashfi Sadabad, Stanford, CA (US); Tulio A. Valdez, Stanford, CA (US); Anping Xia, Stanford, CA (US)

(73) Assignee: The Board of Trustees of the Leland Stanford, Junior University, Stanford, CA (US)

( * ) Notice: Subject to any disclaimer, the term of this patent is extended or adjusted under 35 U.S.C. 154(b) by 447 days.

(21) Appl. No.: 18/132,290

(22) Filed: Apr. 7, 2023

(65) Prior Publication Data

US 2023/0285294 A1 Sep. 14, 2023

Related U.S. Application Data

(63) Continuation of application No. PCT/US2021/044155, filed on Aug. 2, 2021.

(60) Provisional application No. 63/092,497, filed on Oct. 15, 2020.

(51) Int. Cl.

| | |
|---|---|
| ***A61K 9/127*** | (2025.01) |
| ***A61K 9/00*** | (2006.01) |
| ***B82Y 5/00*** | (2011.01) |
| ***B82Y 30/00*** | (2011.01) |

(52) U.S. Cl.

CPC ............ *A61K 9/127* (2013.01); *A61K 9/0046* (2013.01); *B82Y 5/00* (2013.01); *B82Y 30/00* (2013.01)

(58) Field of Classification Search

CPC ................................ A61K 9/0046; B82Y 5/00

See application file for complete search history.

(56) References Cited

U.S. PATENT DOCUMENTS

| | | | |
|---|---|---|---|
| 8,197,461 B1 | 6/2012 | Arenberg et al. | |
| 2006/0008519 A1 | 1/2006 | Davidsen et al. | |
| 2008/0124385 A1 | 5/2008 | Campbell | |
| 2008/0160601 A1 | 7/2008 | Handique | |
| 2013/0289353 A1 | 10/2013 | Seth et al. | |
| 2017/0119803 A1 | 5/2017 | Koyakutty et al. | |
| 2020/0055905 A1 | 2/2020 | Madsen, II et al. | |
| 2020/0345630 A1* | 11/2020 | Joshi .................... | A61K 9/0046 |

FOREIGN PATENT DOCUMENTS

TW I450732 B * 9/2014

OTHER PUBLICATIONS

English machine translation of TW I450732 B made Jun. 11, 2026. (Year: 2026).*

US Patent and Trademark Office, International Search Report and Written Opinion for associated International Application No. PCT/US2021/055155, Jan. 26, 2022, 10 pages.

* cited by examiner

*Primary Examiner* — Michael B. Pallay

(74) *Attorney, Agent, or Firm* — William A English; Vista IP Law Group LLP

(57) ABSTRACT

This application relates to various methods, agents, and systems for delivery of imaging and therapeutic agents to the middle and inner ear. On one aspect, there is a formulation provided in an ear drop form factor based on liposomal nanoparticles that penetrate the eardrum without an incision and can deliver therapeutic agents and/or contrast agents to the middle ear or therapeutic medications to the inner ear.

19 Claims, 22 Drawing Sheets

The Middle Ear
FIG. 2A
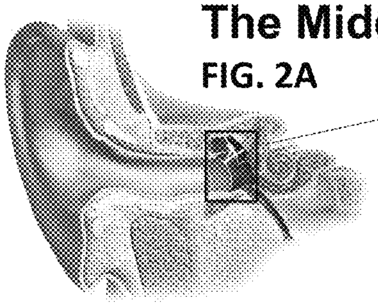
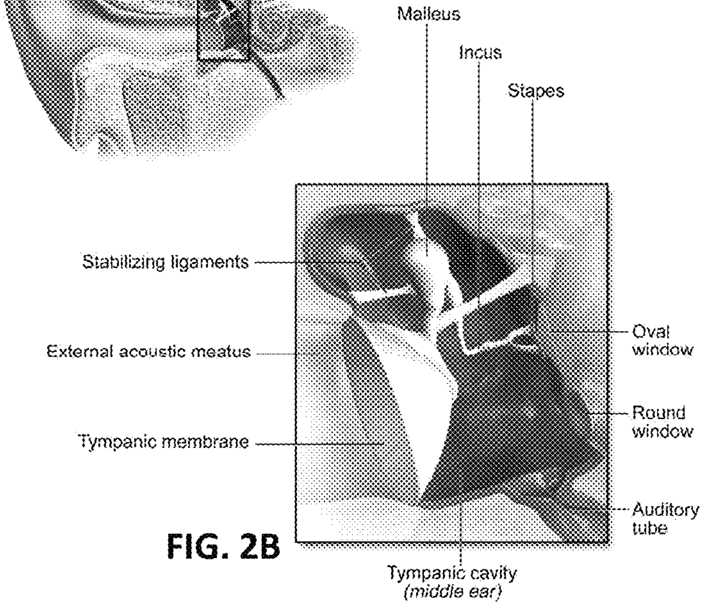
FIG. 2B

FIG. 3A
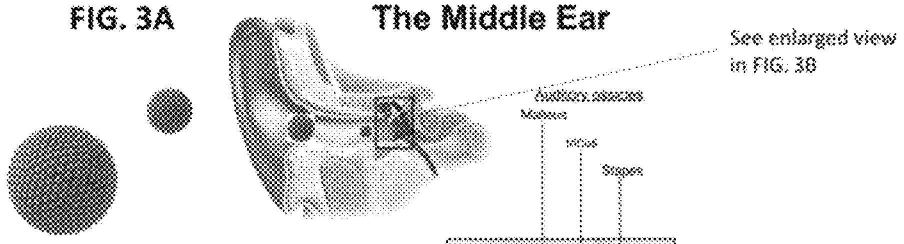
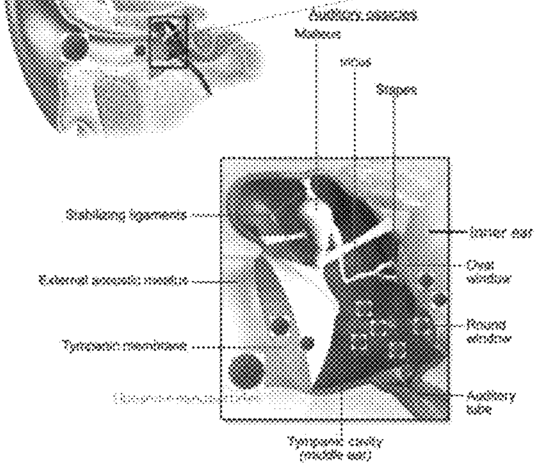
FIG. 3B

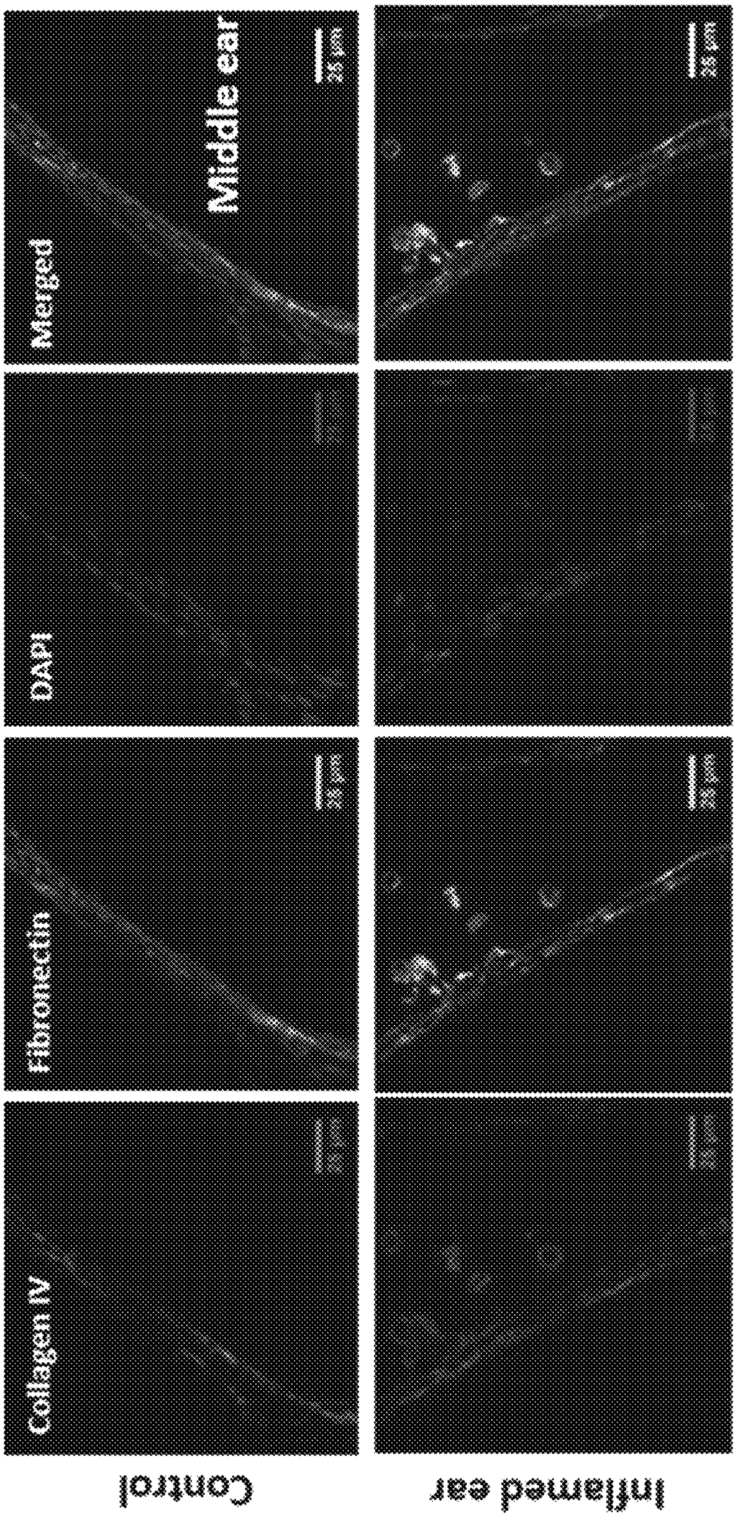
Fig. 7A (top)
FIG. 8A (bottom)
Fig. 7B (top)
FIG. 8B (bottom)
Fig. 7C (top)
FIG. 8C (bottom)
Fig. 7D (top)
FIG. 8D (bottom)

TF-Before freeze drying

TF-After freeze drying

TF-RhB- After freeze drying

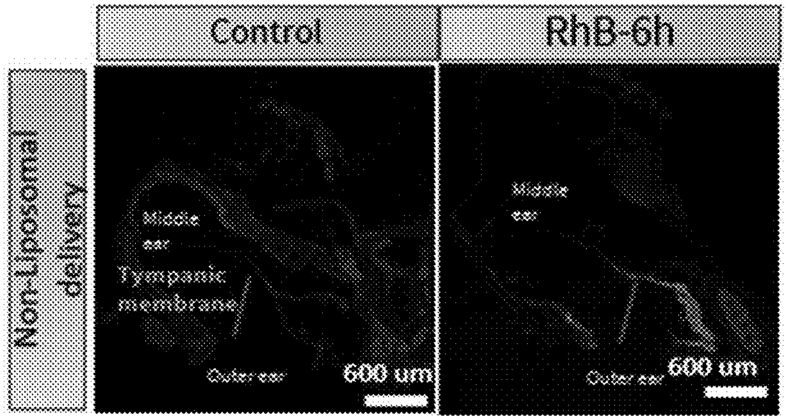
FIG. 10A FIG. 10B
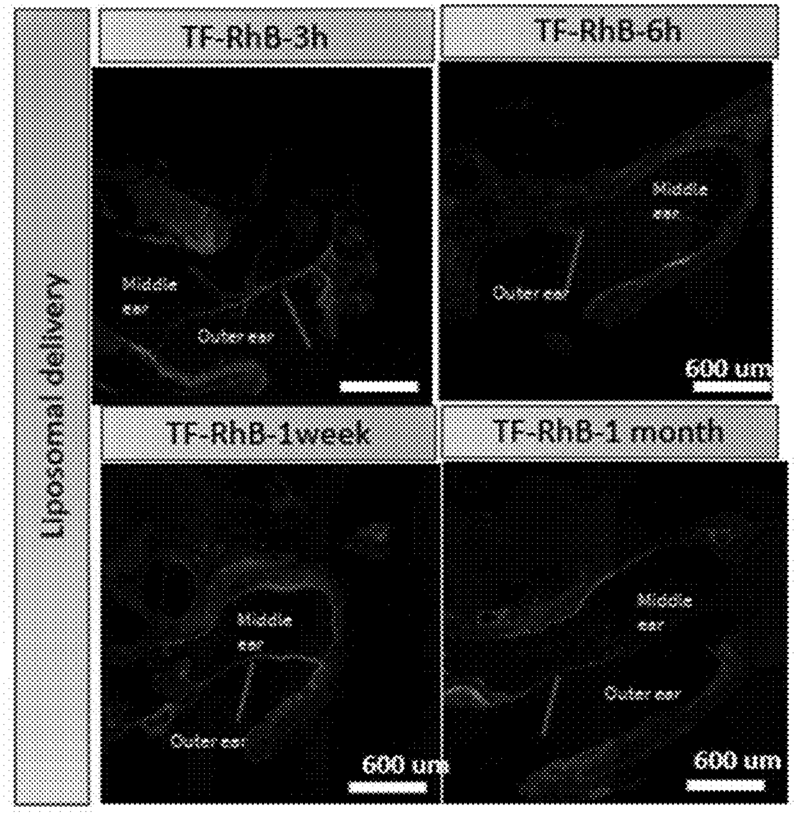
FIG. 11A (top) FIG. 11B (top)
FIG. 11C (bottom) FIG. 11D (bottom)

Liposomal formulation- B1 -6h

Liposomal formulation- B1 -6h

Liposomal formulation- B1 -6h

Liposomal formulation- B1 -24h

METHOD AND SYSTEM FOR OTOTOPICAL DELIVERY USING NANOPARTICLES FOR EAR INFECTION DIAGNOSIS AND TREATMENT

CROSS REFERENCE TO RELATED APPLICATIONS

This application is a continuation of co-pending International Application No. PCT/US2021/044155, filed Oct. 15, 2021, which claims the benefit of U.S. Provisional Patent Application No. 63/092,497, filed Oct. 15, 2020, titled "METHOD AND SYSTEM FOR OTOTOPICAL DELIVERY USING NANOPARTICLES FOR EAR INFECTION DIAGNOSIS AND TREATMENT," the entire disclosures of which are herein incorporated by reference.

STATEMENT AS TO FEDERALLY SPONSORED RESEARCH

This invention was made with Government support under contract TR003142 awarded by the National Institutes of Health. The Government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to methods, formulations and systems for delivery of imaging and therapeutic agents to the middle or inner ear.

BACKGROUND

Clinical diagnosis and treatment of ear infections is a $4 Billion market. In particular, otitis media (OM, inflammation in the middle ear) is one of the most common illnesses among children under five years of age. It is known to affect about 90% of children worldwide. Only in the US, 2.2 million cases of OM are diagnosed annually at a cost of $4 billion. Accurate diagnosis and treatment of OM is critical as it can lead to additional complications such as speech and language development delays, brain abscesses, meningitis, and permanent hearing loss. Additional information is provided in the infographic of FIG. 4.

There are several current standards of diagnosis and treatment for persistent OM however each has a variety of limitations.

One mode of diagnosis for detecting the presence of fluid in the middle ear by pneumatic otoscopy using a light, magnifying lenses to examine monitor the motion of the eardrum in response to a puff of air. This method is subject to erroneous interpretation by the practitioner and thus highly prone to error. However, this mode remains the current standard of practice.

Still another conventional mode includes treatment by surgical insertion of a tube into the tympanic membrane (TM) and removal the thick fluid by suction. This procedure suffers from the shortcomings of requiring general anesthesia and multiple post-operative check-ups until the tube extrudes and the tympanic membrane heals.

Still another conventional mode includes treatment by antibiotic administration. It is common to use the delivery modes of systemic intravenous injection or oral administration. However, these delivery modes suffer from non-specific biodistribution and frequently require high-dosage administration.

What is needed are improvements in the diagnosis and treatment of middle and inner ear disorders.

SUMMARY OF THE DISCLOSURE

In general, in one embodiment, a method of detecting or treating a disorder in an ear of a patient includes delivering an ear drop containing a nanoparticle having at least one of an imaging agent, a diagnostic agent, or a therapeutic agent into the ear canal of the patient, penetrating without damaging the tympanic membrane or round window with the nanoparticle, and delivering the agent or agents to the middle ear or the inner ear of the patient for the detection or treatment of a disorder of ear of the patient.

This and other embodiments can include one or more of the following features. Multiple imaging agents, diagnostic agents, or therapeutic agents can be delivered by the same nanoparticle. The nanoparticle can be adapted for detection or treatment of otitis media. The nanoparticle can be adapted for detection or changing properties of fluid as part of a diagnosis or treatment of otitis media with effusion. The nanoparticle can be adapted for detection or eradication of infection in fluid as part of a diagnosis or treatment of acute or chronic otitis media. The imaging agent can include an inflammation targeted probe that will fluoresce further including a step of detecting a presence of a fluid and/or an indication of whether the fluid is infected. The probe can fluoresce within the visible, NIR and short-wave infrared spectrum. The nanoparticle can be a lipid-based or liposomal formulation.

In general, in one embodiment, a liposomal nanoparticle for delivery to structures of the middle or inner ear includes a vesicular structure composed of lipids arranged in a shell-like bilayer formulated for trans-tympanic membrane delivery, and at least one of an imaging agent, a diagnostic agent, or a therapeutic agent loaded onto the structure.

This and other embodiments can include one or more of the following features. The liposomal nanoparticle can further include a formulation adapted for delivery of mucolytic or anti-microbial drugs to the middle ear. The liposomal nanoparticle can further include a formulation adapted for delivery of therapeutic or protective agents to the inner ear. The liposomal nanoparticle can further include a formulation including multiple compounds loaded simultaneously on, in or within the liposomal nanoparticle. The lipids can include phospholipids. The lipids can include a hydrophilic surface and core and a hydrophobic interior of the shell like bi-layer. The at least one of the imaging agents, the diagnostic agent or the therapeutic agent can be loaded on, in or within a portion of a hydrophilic surface, a hydrophilic core, or interior or combinations thereof. The liposomal nanoparticle can be formulated as an ear drop.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2A is a cross section view of an inner ear.

FIG. 2B is an enlarged portion of the cross-section view of FIG. 2A showing the relationship of the tympanic membrane, the tympanic cavity or middle ear, the oval window, the round window and a portion of the inner ear beyond the oval window and the round window.

FIG. 3A is a cross section view of the ear as in FIG. 2A with a nanoparticle embodiment inserted into the ear canal.

FIG. 3B is an enlarged portion of the cross-section view of FIG. 3A showing the relationship of the tympanic membrane, the tympanic cavity or middle ear, the oval window, the round window and a portion of the inner ear beyond the oval window and the round window along with the atraumatic passage of various nanoparticle particles.

FIGS. 7A, 7B, 7C and 7D are control images of a non-inflamed or a healthy tympanic membrane, showing imaging specificity of Collagen IV in FIG. 7A, Fibronectin in FIG. 7B, DAPI in FIG. 7C and in FIG. 7D an image representing a merged image of FIGS. 7A, 7B and 7C.

FIG. 7D also indicates the location of the middle ear with respect to the healthy tympanic membrane.

FIGS. 8A, 8B, 8C and 8D correspond to the control image sequence in FIGS. 7A-7D of a healthy tympanic membrane but now imaging an inflamed tympanic membrane. FIG. 8A is showing imaging specificity of Collagen IV, Fibronectin in FIG. 8B, DAPI in FIG. 8C and in FIG. 8D an image representing a merged image of FIGS. 8A, 8B and 8C. FIG. 8D also indicates the location of the middle ear with respect to the inflamed tympanic membrane.

FIGS. 10A and 10B are confocal images of an eardrum or tympanic membrane before treatment with non-liposomal delivery of RhB fluorescent dye (FIG. 10A) and after 6 hours (FIG. 10B) which did not show any penetration into the middle ear as in FIGS. 11A-11D.

FIGS. 11A-11D are confocal images of an eardrum or tympanic membrane similar to the control images in FIG. 10A after treatment with liposomal delivery of RhB fluorescent dye showing the delivery of the RhB dye into the middle ear and increased accumulation at 3 hours (FIG. 11A), after 6 hours (FIG. 11B), after 1 week (FIG. 11C) and after 1 month (FIG. 11D) in contrast to the control image FIG. 10B which did not show any penetration into the middle ear for the non-liposomal formulation of RhB.

FIG. 12A is showing imaging specificity of DAPI in blue. FIG. 12B is showing imaging specificity to TF-RhB in red. FIG. 12C is a differential interference contrast (DIC) image. FIG. 12D is showing a color composite overlay of the images in FIGS. 12A, 12B, and 12C.

FIG. 13A is showing imaging specificity of DAPI. FIG. 13B is showing imaging specificity to TF-RhB. FIG. 13C is a differential interference contrast (DIC) image. FIG. 13D is showing a composite overlay of the images in FIGS. 13A, 13B, and 13C.

FIG. 14A is showing imaging specificity of DAPI in blue. FIG. 14B is showing imaging specificity to TF-RhB in red. FIG. 14C is a differential interference contrast (DIC) image. FIG. 14D is showing a color composite overlay of the images in FIGS. 14A, 14B, and 14C.

FIG. 15A is showing imaging specificity of TF-RnB in red. FIG. 15B is showing imaging specificity to DAPI in blue. FIG. 15C is showing a color composite overlay of the images in FIGS. 15A and 15B.

FIG. 16A is showing imaging specificity of TF-RnB in red. FIG. 16B is showing imaging specificity to DAPI in blue. FIG. 16C is showing a color composite overlay of the images in FIGS. 16A and 16B.

FIG. 22A is showing imaging specificity of DAPI in blue. FIG. 22C is showing imaging specificity to TF-RhB in red. FIG. 22B is a differential interference contrast (DIC) image. FIG. 22D is showing a color composite overlay of the images in FIGS. 12A, 12B, and 12C.

DETAILED DESCRIPTION

In one aspect of the present invention, there is provided a method and system for delivering imaging agents, therapeutic agents, or both in a single formulation to the middle or inner ear area using nanoparticles that can pass through the tympanic membrane (i.e., eardrum).

Figure 5A:
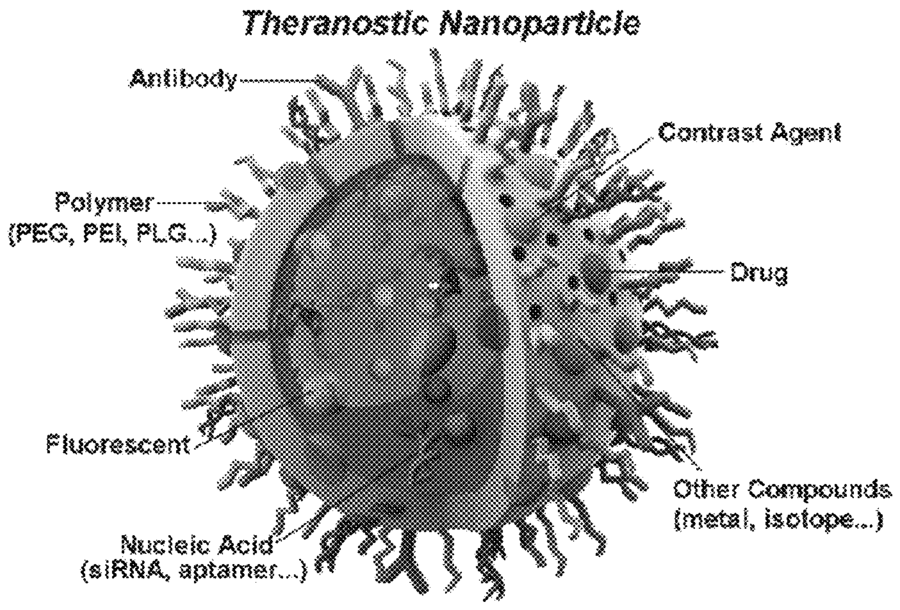
FIG. 5A is a partial section view of an exemplary nanoparticle which may be used for theranostic approaches.

FIG. 5A is a partial section view of an exemplary nanoparticle which may be used for theranostic approaches. Particles in the nanometer scale have advantages in a range of medical applications because of the size. One nanometer (nm) is one billionth of a meter. Put another way, one nanometer is about $1/1000^{th}$ of the width of a human hair which has a width of about 100 microns. Importantly, compositions within this size scale will not clog the blood stream, can get into cells and provide a large surface area to volume ratio. Additionally, exemplary nanoparticles of some embodiments of the present invention may be used to combine therapeutic compositions with an imaging agent or other combinations as shown in the example of FIG. 5A. Still further, the specific formulation of the nanoparticle may be optimized for targeted delivery of one or more drugs into specific tissue. Moreover, the exemplary theranostic nanoparticle in FIG. 5A is illustrative of the multiple functions that may be designed into a specific nanoparticle to deliver one or a combination of different payloads.

Figure 5B:
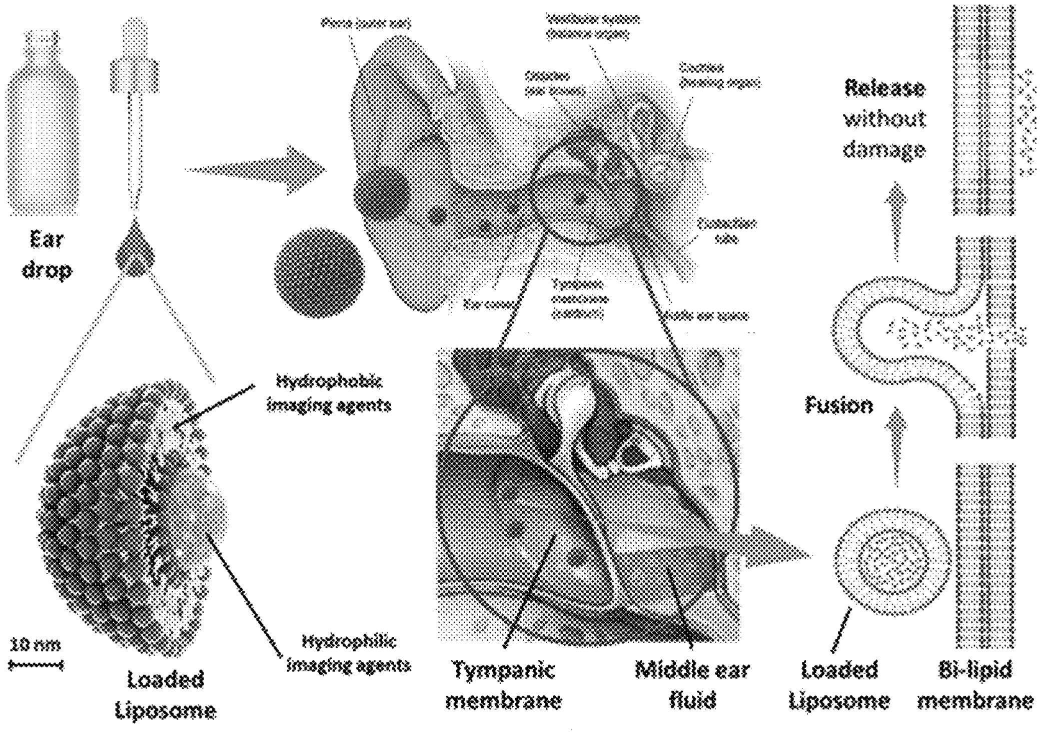
FIG. 5B is an infographic diagram representing an exemplary loaded liposome nanoparticle compound and pathway for the nanoparticle to enter the middle ear.

FIG. 5B is an infographic diagram representing an exemplary loaded liposome nanoparticle compound and pathway for the nanoparticle to enter the middle ear. The exemplary loaded liposome may include one or more imaging agents such as a hydrophobic imaging agent or a hydrophilic imaging agent alone or in any combination.

The anatomy of the human ear is provided in the views of FIGS. 2A and 2B. FIG. 2A is a cross section view of an inner ear. FIG. 2B is an enlarged portion of the cross-section view of FIG. 2A showing the relationship of the tympanic membrane, the tympanic cavity or middle ear, the oval window, the round window and a portion of the inner ear beyond the oval window and the round window. As used herein, penetration, translation or delivery of nanoparticle comprising formulations as described herein include the introduction into the ear canal and subsequent movement of the formulation beyond the tympanic membrane in furtherance of a therapeutic effect, a diagnostic effect or a combination thereof on, in or within the middle ear or a structure thereof, or, optionally or additionally, in treatment of a structure or disorder beyond the middle ear via atraumatic translation through and beyond one or both of the oval window or the round window. In some embodiments, the "round window" is a second barrier that embodiments of the nanoparticle described herein will must pass without damaging so as to translate from middle ear to inner ear.

In the description that follows, it is to be appreciated that one can load the agents anywhere on the nanoparticle, including hydrophilic surface, hydrophilic core, or both. As such the agents may be considered broadly as loaded into the nanoparticle structure as variously described herein.

Still further, embodiments of the present invention include an ear drop based on liposomal nanoparticles that penetrate the eardrum and round window membrane (RWM) without an incision and can deliver therapeutic agents and/or contrast agents to the middle ear and inner ear. Advantageously as compared to the conventional methods detailed above, embodiments of the inventive delivery system are inexpensive, painless, and risk-free alternative to surgery and extremely convenience for patients, resulting in fewer doctor visits, reducing cost of care, and improving overall quality of life for children and their parents. In additional alternatives, there are embodiments that provide a health care practitioner with a local delivery pathway including an ability to concentrate therapeutic and imaging agents for middle and inner ear diseases. In still other alternatives, there are provided a wide range of alternative embodiments of this method, using other types of nanoparticle agents, imaging probes, drug molecules, and administrative procedures can be employed for the various uses described herein.

In one aspect, there is provided a formulated and synthesized a liposomal nanoparticle carrier. In a specific embodiment, there are included vesicular structures composed of phospholipids arranged in a shell-like bilayer with a hydrophilic surface (facing aqueous solution) and hydrophobic interior. Embodiments of this shell-like structure makes liposomes ideal carriers, enabling loading or encapsulation of drug molecules. The ability of the inventive embodiments to fuse (at nanoscale) with lipid-rich barriers in the tympanic membrane enables liposomes to push the cargo (e.g., imaging probes or drug molecules) through without damaging those barriers. Embodiments of the liposomes as described herein are biocompatible (i.e., non-toxic) and bio-degradable, in formulations safe for administration to pediatric patients. Safe as used herein refers to meeting those standards used for liposomes when first FDA-approved as nanomedicines for clinical trials in the 1990s. In still further embodiments, the inventive liposomes are adapted liposomal nano-formulations suited for trans-tympanic delivery. In this context, suited for trans-tympanic delivery refers to embodiment that can carry encapsulated/conjugated therapeutic and contrast agents through the TM alone or in combination with the RWM for therapeutic or diagnostic applications in disorders of the middle ear and inner ear or other disease states.

Figure 6:
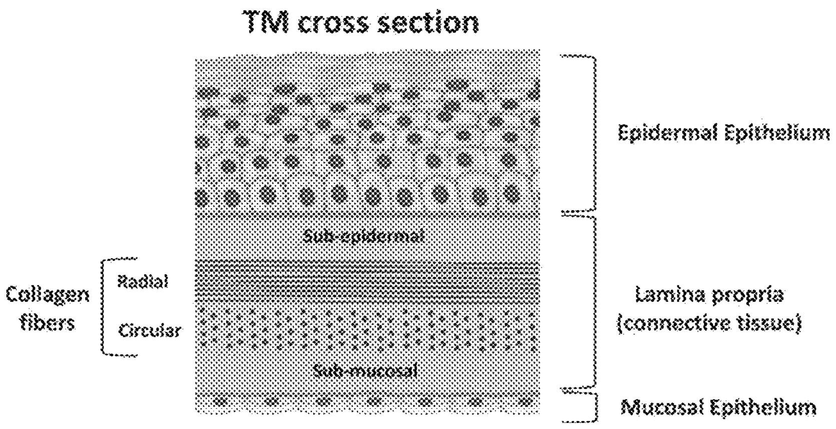
FIG. 6 is a microscopic cross section of a tympanic membrane having an outer layer with an epidermal epithelium, a central connective layer including lamina propria with radial and circular collagen fibers and an inner layer or the mucosal epithelium.

While desiring not to be bound by theory, it is believed that the tympanic membrane has a similar structure and penetration barriers like the skin consisting of keratin and a lipid-rich stratum corneum. FIG. 6 is a microscopic cross section of a tympanic membrane having an outer layer with an epidermal epithelium, a central connective layer including lamina propria with radial and circular collagen fibers and an inner layer or the mucosal epithelium.

The RWM consists of three layers: an outer epithelial layer facing the middle ear, a central connective tissue layer, and an inner epithelial layer. The evidence shows the RWM permeability allows passage of a wide range of materials including antibiotics, local anesthetics, toxins, and albumin. As such, it is believed that liposomal nanoparticles suited for topical delivery (i.e., delivery through skin) may be well suited and are adapted in these various formulations and embodiment for various applications of ototopical delivery (i.e., delivery through eardrum) for diagnostic, therapeutic, imaging or other payloads as described herein, or any of those in FIG. 5A.

FIG. 3A is a cross section view of the ear as in FIG. 2A with a nanoparticle embodiment inserted into the ear canal as described herein.

FIG. 3B is an enlarged portion of the cross-section view of FIG. 3A showing the relationship of the tympanic membrane, the tympanic cavity or middle ear, the oval window, the round window and a portion of the inner ear beyond the oval window and the round window. This view also illustrates the atraumatic passage of various nanoparticle particles into the middle and inner ear without damage to structures of the ear while also delivering the payload of a particular nanoparticle formulation.

In still other embodiments, aspects of the present invention may be provided in a form factor allowing use as an ear drop that can be administered clinically by physicians or other health practitioners in the care of pediatric patients using a non-invasive diagnosis and treatment of their middle ear infections. In still further embodiments, there is provided a method for diagnosis and treatment of other middle/inner ear related diseases in a convenient, cost-effective, and painless fashion including additional formulations incorporated into a trans-tympanic liposomal formulation including agents developed by pharmaceutical companies or biotech companies. Additionally or optionally, the advantageous trans-tympanic formulations and techniques may can be used for combined diagnosis and therapy (i.e., using one agent to do both) as well as multi-functional diagnosis or therapy (i.e., delivering one or more probes or drugs with different properties, e.g., inserting hydrophobic molecule within the shell layers and encapsulating hydrophilic molecules at the core and/or loading them on the surface, within the same liposomal carrier). One exemplary ear related disease suited for treatment using an embodiment of the present invention includes sensorineural hearing loss (SNHL).

FIGS. 7A, 7B, 7C and 7D along with FIGS. 8A, 8B, 8C and 8D are the result imaging studies related to changes of the tympanic membrane as a result of inflammation.

FIGS. 7A, 7B, 7C and 7D are control images of a non-inflamed or a healthy tympanic membrane, showing imaging specificity of Collagen IV in FIG. 7A, Fibronectin in FIG. 7B, DAPI in FIG. 7C and in FIG. 7D an image representing a merged image of FIGS. 7A, 7B and 7C. FIG. 7D also indicates the location of the middle ear with respect to the healthy tympanic membrane.

FIGS. 8A, 8B, 8C and 8D correspond to the control image sequence in FIGS. 7A-7D of a healthy tympanic membrane but now imaging an inflamed tympanic membrane. FIG. 8A is showing imaging specificity of Collagen IV, Fibronectin in FIG. 8B, DAPI in FIG. 8C and in FIG. 8D an image representing a merged image of FIGS. 8A, 8B and 8C. FIG. 8D also indicates the location of the middle ear with respect to the inflamed tympanic membrane.

In one illustrative embodiment, liposomal vesicles formulation, synthesis, and characterization were fabricated as follows: First, there was a thin-film hydration followed by extrusion method to form elastic liposomal vesicles. Soybean phosphatidylcholine (PC) with purity >99% and sodium cholate were used as lipid source and as surfactant to enhance the elasticity of the liposomes respectively. The obtained vesicles were downsized by passing through an extruder system equipped to a polycarbonate filter with 100 nm pore size. The filtrated transferosomes were lyophilized in presence of sucrose to avoid any undesirable aggregation/fusion.

The vesicles size distribution was then evaluated as shown in FIGS. 9A-9F.

Figure 9A:
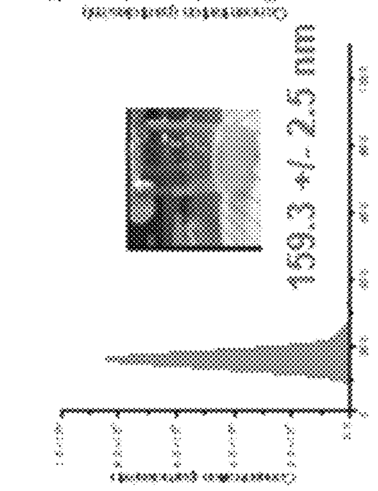
FIG. 9A illustrates a representative vesicles size distribution in an exemplary formulation before freeze-drying.

FIG. 9A illustrates a representative vesicles size distribution in an exemplary formulation before freeze-drying. FIG. 9B is a cryo-TEM image of tranferesome vesicles of FIG. 9A before freeze-drying.

Figure 9C:
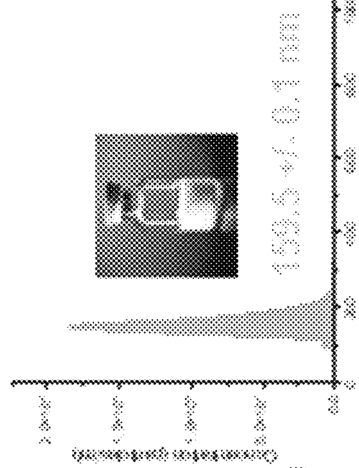
FIG. 9C illustrates a representative vesicles size distribution in the exemplary formulation of FIG. 9A after freeze-drying.

FIG. 9C illustrates a representative vesicles size distribution in the exemplary formulation of FIG. 9A after freeze-drying. FIG. 9D is a cryo-TEM image of tranferesome vesicles of FIG. 9C after freeze-drying.

Figure 9E:
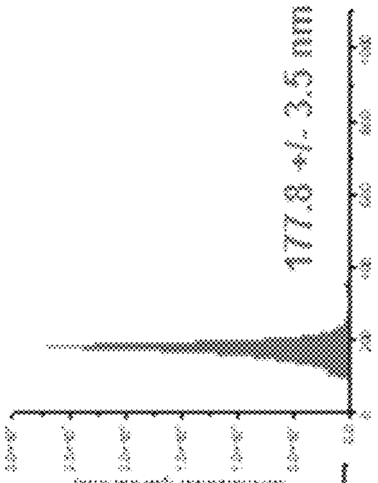
FIG. 9E illustrates a representative vesicles size distribution in the exemplary formulation of FIG. 9A encapsulated with RhB fluorescent dye after freeze-drying.
Figure 9B:
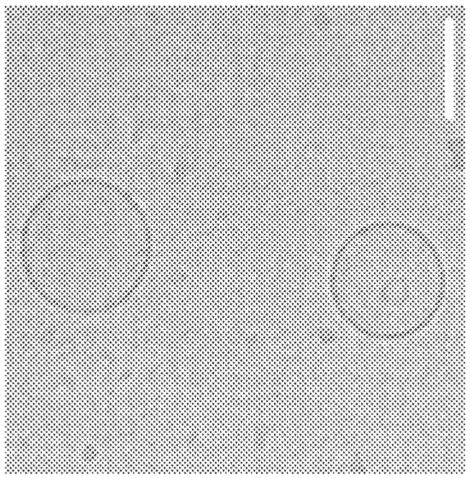
FIG. 9B is a cryo-TEM image of tranferesome vesicles of FIG. 9A before freeze-drying.
Figure 9D:
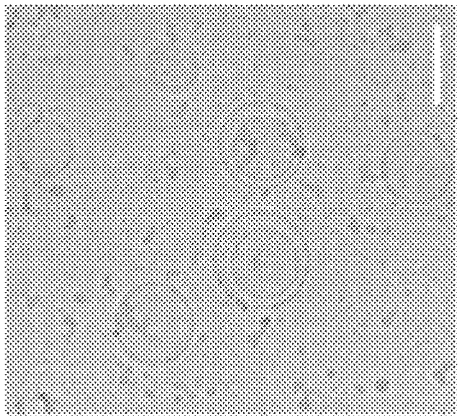
FIG. 9D is a cryo-TEM image of tranferesome vesicles of FIG. 9C after freeze-drying.
Figure 9F:
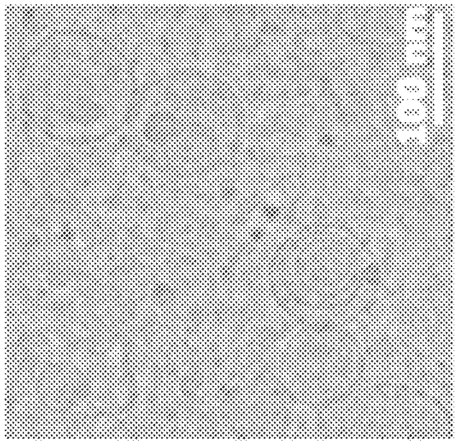
FIG. 9F is a cryo-TEM image of tranferesome vesicles of FIG. 9E after freeze-drying showing vesicles with an apparent size of around 120 nm and without aggregation after freeze-drying and encapsulation with the fluorescent RnB dye.

FIG. 9E illustrates a representative vesicles size distribution in the exemplary formulation of FIG. 9A encapsulated with RhB fluorescent dye after freeze-drying. FIG. 9F is a cryo-TEM image of tranferesome vesicles of FIG. 9E after freeze-drying showing vesicles with an apparent size of around 120 nm and without aggregation after freeze-drying and encapsulation with the fluorescent RnB dye.

Cryo-TEM images described above showed uniform and unilamellar formation of vesicles with apparent size at around 120 nm and confirmed the vesicles stayed intact without any aggregation after freeze-drying and encapsulation with the fluorescent RhB-dye.

FIGS. 10A and 10B are confocal images of an eardrum or tympanic membrane before treatment with non-liposomal delivery of RhB fluorescent dye (FIG. 10A) and after 6 hours (FIG. 10B) which did not show any penetration into the middle ear as in FIGS. 11A-11D.

FIGS. 11A-11D are confocal images of an eardrum or tympanic membrane similar to the control images in FIG. 10A after treatment with liposomal delivery of RhB fluorescent dye showing the delivery of the RhB dye into the middle ear and increased accumulation at 3 hours (FIG. 11A), after 6 hours (FIG. 11B), after 1 week (FIG. 11C) and after 1 month (FIG. 11D) in contrast to the control image FIG. 10B which did not show any penetration into the middle ear for the non-liposomal formulation of RhB.

Further consideration of the various images in FIGS. 10A-11D one may observe from these confocal images of eardrum and vesicles penetration into the middle ear at different time points. To verify the permeation of the formulated vesicles through the eardrum we looked at the ear sections under confocal microscopy. In the animal receiving TF-RhB, red spheres were detected at different layers of the eardrum as well as in the middle ear 3 h post-treatment (FIG. 11A) indicating rapid distribution and penetration to the ear cavity. We did not observe any fluorescent from pure RhB in the middle ear cavity (FIGS. 10A, 10B) showing the significant role of liposomal vesicles in carrying the dye to the middle ear. Moreover, at 6 h post-treatment a significant amount of the vesicles was observed in the middle ear showing accumulation of the vesicles in the middle ear over time. (See FIG. 11B). Also confirmed in the 1 week and 1 month images of FIGS. 11C and 11D.

FIGS. 12A-14D relate to a series of confocal imaging at higher magnification of tympanic membrane. The TF-RhB shows particles penetrations from different layers of tympanic membrane (see FIG. 12D) whereas RhB without nanoparticles formulation stays on the surface of tympanic membrane without any penetration (see FIG. 14D).

Figures 12A, 12B, 12C, 12D:
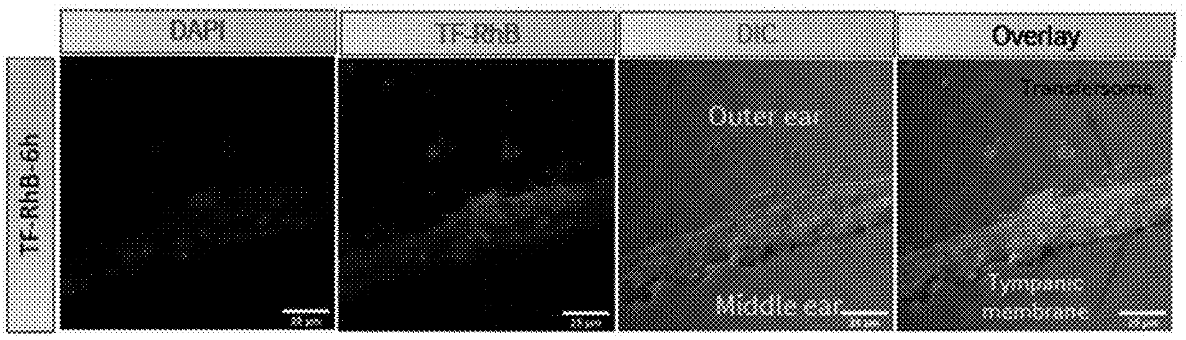
FIGS. 12A, 12B, 12C and 12D correspond to an image sequence for a tympanic membrane exposed to a liposomal formulation of RnB dye showing that RnB dye is present in the middle ear after 6 hours in contrast to the absence of RhB using a non-liposomal approach as in FIGS. 14A-14D.
Figures 13A, 13B, 13C, 13D:
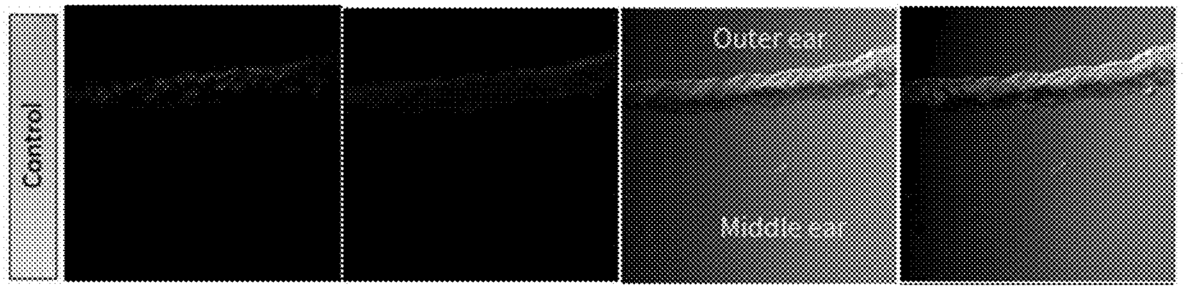
FIGS. 13A, 13B, 13C and 13D correspond to the control image sequence for a tympanic membrane as in the images in FIGS. 12A-12D and 14A-14D.

FIGS. 13A, 13B, 13C and 13D correspond to the control image sequence of a healthy tympanic membrane. FIG. 13A is showing imaging specificity of DAPI, TF-RhB in red in FIG. 12B, DIC in FIG. 12C and in FIG. 12D an image representing a merged image of FIGS. 12A, 12B, 12C and 12D.

FIGS. 12A, 12B, 12C and 12D correspond to an image sequence for a tympanic membrane exposed to a liposomal formulation of RnB dye showing that RnB dye is present in the middle ear after 6 hours in contrast to the absence of RhB using a non-liposomal approach as in FIGS. 14A-14D. FIG. 12A is showing imaging specificity of DAPI in blue. FIG. 12B is showing imaging specificity to TF-RhB in red. FIG. 12C is a differential interference contrast (DIC) image. FIG. 12D is showing a color composite overlay of the images in FIGS. 12A, 12B, and 12C.

FIGS. 13A, 13B, 13C and 13D correspond to the control image sequence for a tympanic membrane as in the images in FIGS. 12A-12D and 14A-14D. FIG. 13A is showing imaging specificity of DAPI. FIG. 13B is showing imaging specificity to TF-RhB. FIG. 13C is a differential interference contrast (DIC) image. FIG. 13D is showing a composite overlay of the images in FIGS. 13A, 13B, and 13C.

Figures 14A, 14B, 14C, 14D:
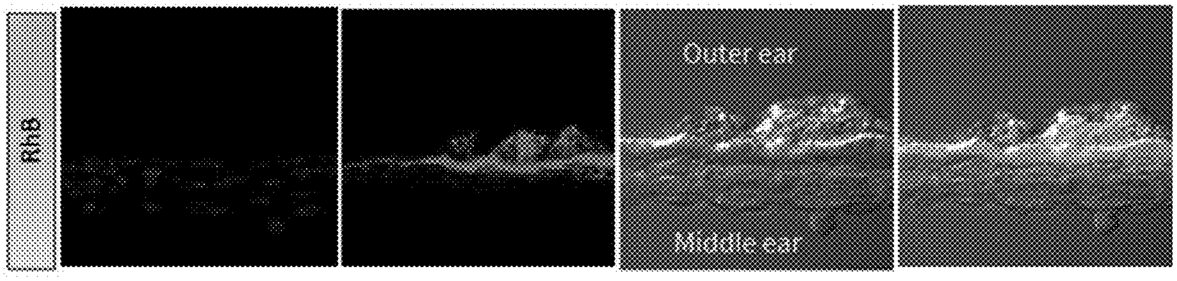
FIGS. 14A, 14B, 14C and 14D correspond to an image sequence for a tympanic membrane exposed to a non-liposomal formulation of RnB dye showing that RnB dye is not present in the middle ear after delivery in contrast to FIG. 12D and a liposomal approach.

FIGS. 14A, 14B, 14C and 14D correspond to an image sequence for a tympanic membrane exposed to a non-liposomal formulation of RnB dye showing that RnB dye is not present in the middle ear after delivery in contrast to FIG. 12D and a liposomal approach. FIG. 14A is showing imaging specificity of DAPI in blue. FIG. 14B is showing imaging specificity to TF-RhB in red. FIG. 14C is a differential interference contrast (DIC) image. FIG. 14D is showing a color composite overlay of the images in FIGS. 14A, 14B, and 14C.

Figures 15A, 15B, 15C:
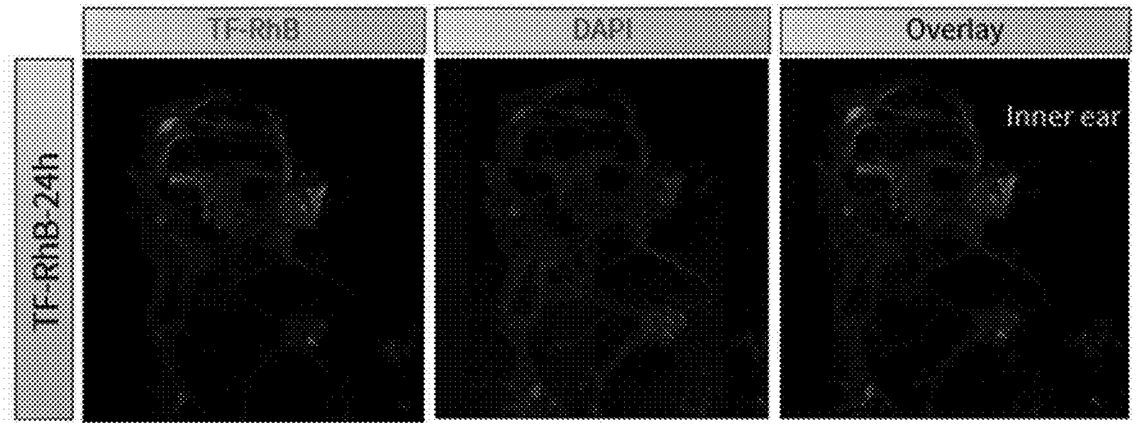
FIGS. 15A, 15B, and 15C correspond to an image sequence for a tympanic membrane exposed to a liposomal formulation of RnB dye showing that RnB dye is present in the middle ear after 24 hours as compared to the control images in FIGS. 16A, 16B and 16C.
Figures 16A, 16B, 16C:
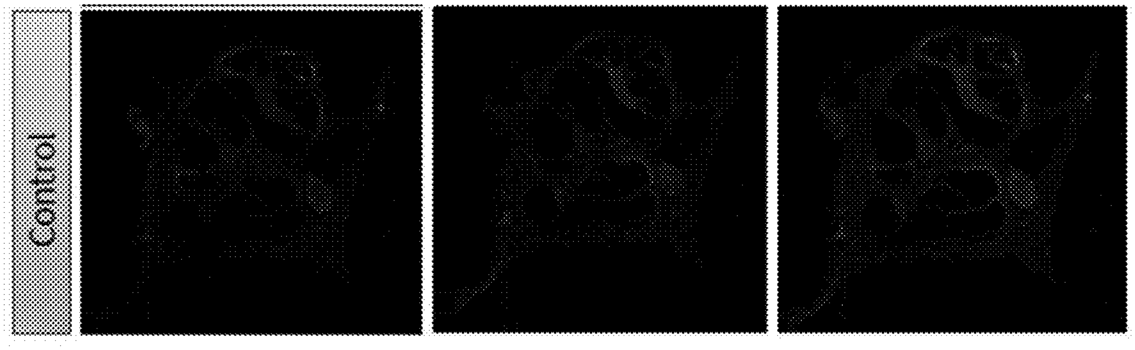
FIGS. 16A-16C are control images for FIGS. 15A-15C.

FIGS. 15A, 15B, and 15C correspond to an image sequence for a tympanic membrane exposed to a liposomal formulation of RnB dye showing that RnB dye is present in the middle ear after 24 hours as compared to the control images in FIGS. 16A, 16B and 16C. FIG. 15A is showing imaging specificity of TF-RnB in red. FIG. 15B is showing imaging specificity to DAPI in blue. FIG. 15C is showing a color composite overlay of the images in FIGS. 15A and 15B.

FIGS. 16A-16C are control images for FIGS. 15A-15C. FIG. 16A is showing imaging specificity of TF-RnB in red. FIG. 16B is showing imaging specificity to DAPI in blue. FIG. 16C is showing a color composite overlay of the images in FIGS. 16A and 16B.

These confocal images from inner ear show particle penetrations beyond the middle ear to inner ear. (FIG. 15C). As such, it is believed that potential applications of various embodiments of a liposomal nanoparticle may be used for inner ear drug delivery.

Figure 17A:
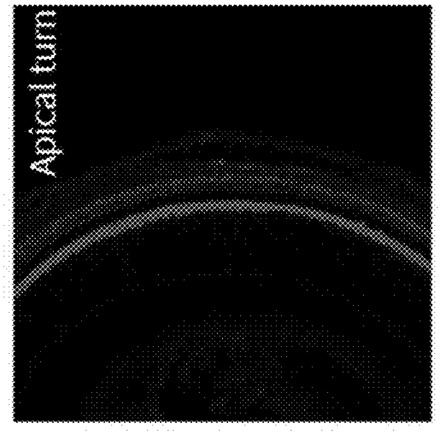
FIGS. 17A, 17B and 17C are confocal microscopy images of an inner ear showing the preservation of hair cells in the Organ of Corti in an apical turn (FIG. 17A), a middle turn (FIG. 17B) and a basal turn (FIG. 17C).
Figure 17B:
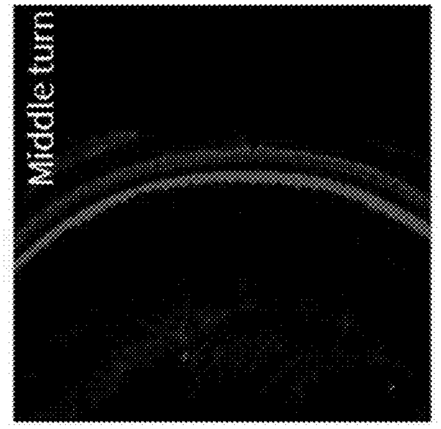
Figure 17C:
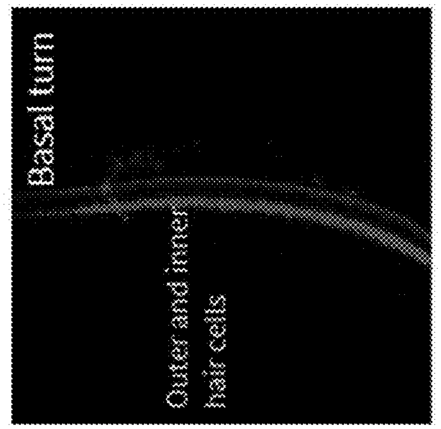

FIGS. 17A, 17B and 17C are confocal microscopy images of an inner ear showing preservation of hair cells.

For analysis of hair cells patterns in the organ of corti, the otic capsule containing the membranous inner ear were dissected out by decapitation and opening of the skull at the midline. The whole inner ear was fixed in 4% PFA in PBS for overnight and decalcified with EDTA solution (100 mM) for three days.

FIGS. 17A, 17B and 17C were taken from samples prepared above. These images demonstrate the preservation of hair cells in the Organ of Corti in an apical turn (FIG. 17A), a middle turn (FIG. 17B) and a basal turn (FIG. 17C).

Figure 18:
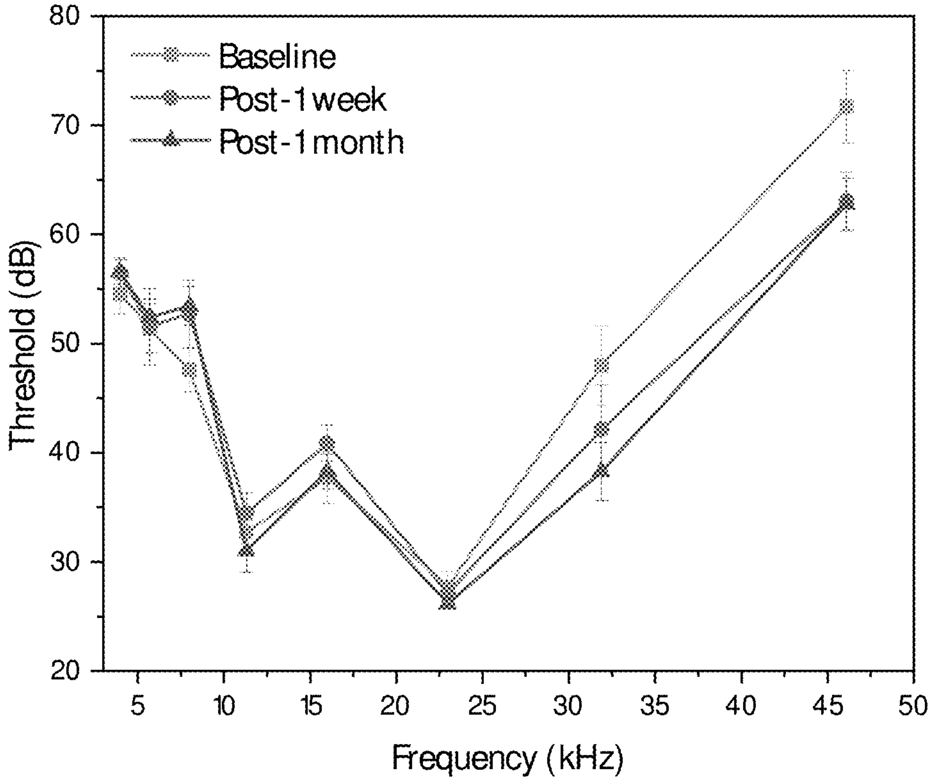
FIG. 18 is a graph of auditory brainstem response in mice of threshold (db) versus frequency (kHz) for mice at baseline, after 1 week of liposomal vesicles administration and after 1 month of liposomal administration.

FIG. 18 is a graph of auditory brainstem response in mice of threshold (db) versus frequency (kHz) for mice at baseline, after 1 week of liposomal vesicles administration and after 1 month of liposomal administration.

We studied long-term effects of our formulation on the functionality of the mice ears by testing their hearing ability via auditory brainstem response (ABR). The results showed that hearing sensitivities remained largely unchanged demonstrating that vesicles neither disturb the function of the inner ear and nor causes hearing impairment in mice.

Figure 19:
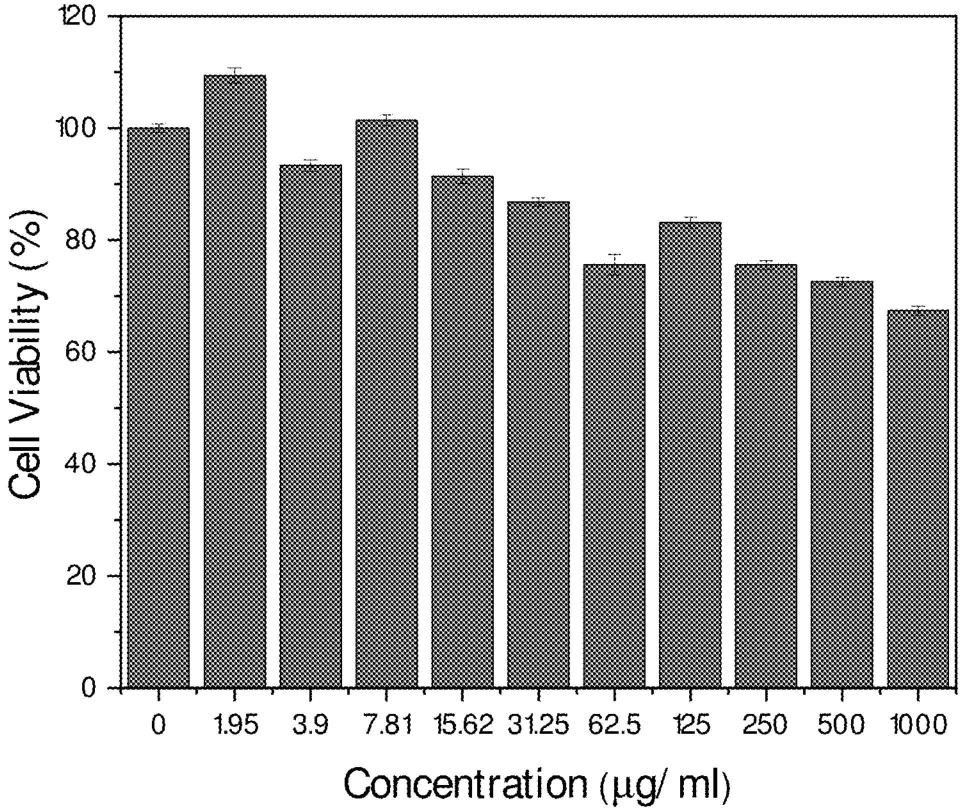
FIG. 19 is a graph of the results of an MTT assay to evaluate cytotoxicity of vocal fold fibroblasts showing cell viability (%) against exposure to vesicles at different concentrations (microgram/milliliter) after 24 hours of incubation.

FIG. 19 is a graph of the results of an MTT assay to evaluate cytotoxicity of vocal fold fibroblasts showing cell viability (%) against exposure to vesicles at different concentrations (microgram/milliliter) after 24 hours of incubation.

We performed an MTT assay to evaluate the safety of the designed formulations for subsequent clinical trials. Vocal fold fibroblasts (VFF) cells were exposed to the vesicles at different concentrations and the viability of the cells was quantified by measuring using a microplate reader. MTT cytotoxicity studies on vocal cells after 24 h of incubation with vesicles. The results indicate that vesicles did not affect the proliferation of the cells, hence are not toxic.

Figure 20A:
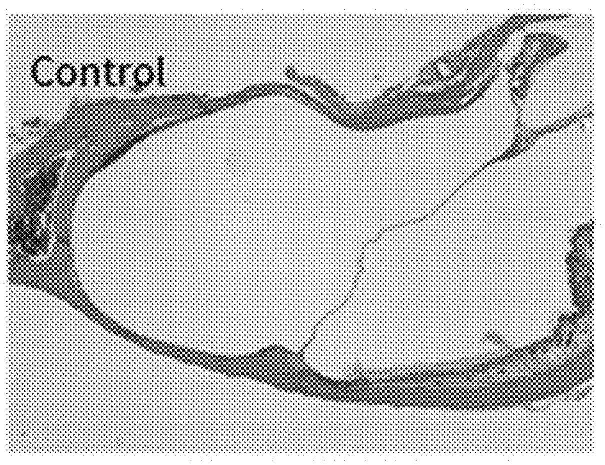
FIGS. 20A and 20B are H&E stained middle sections of a mouse middle ear after 30 days with no vesicles treatment (control in FIG. 20A) and with treatment of vesicles (TF-RnB in FIG. 20B).
Figure 20B:
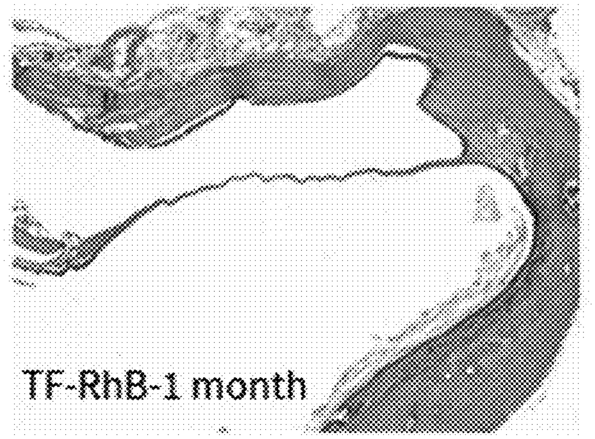

FIGS. 20A and 20B are H&E stained middle sections of a mouse middle ear after 30 days with no vesicles treatment (control in FIG. 20A) and with treatment of vesicles (TF-RnB in FIG. 20B). Formulations were administered to the ear canals of live healthy mice and 30 days later, they were euthanized. Following sacrifice, the middle ear was excised and immediately fixed in 10% neutral buffered formalin overnight, then decalcified, embedded in paraffin, sectioned and stained with H&E.

Figure 21A:
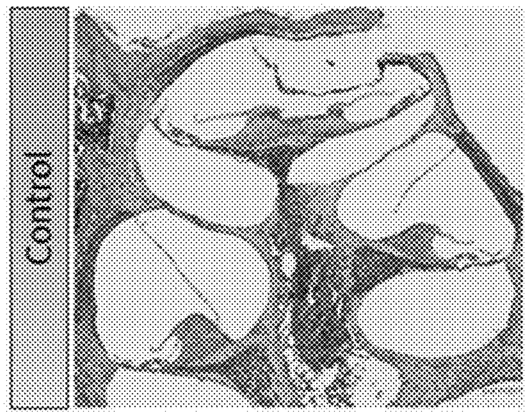
FIGS. 21A and 21C are images of a histology analysis of inner sections before application of a nanoparticle formulation for safety evaluation.
Figure 21C:
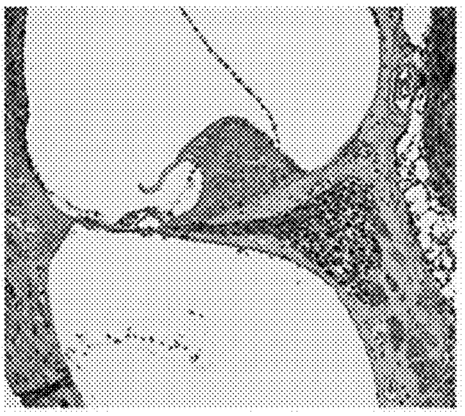

FIGS. 21A and 21C are images of a histology analysis of inner sections before application of a nanoparticle formulation for safety evaluation.

Figure 21B:
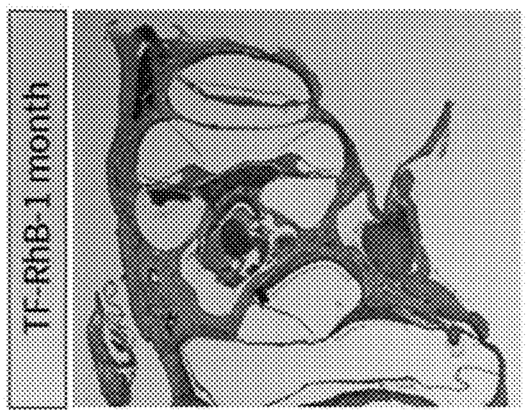
FIGS. 21B and 21D are images of the inner sections of FIGS. 21A and 21C respectively after application of liposomal formulation TF-RnB for one month.
Figure 21D:
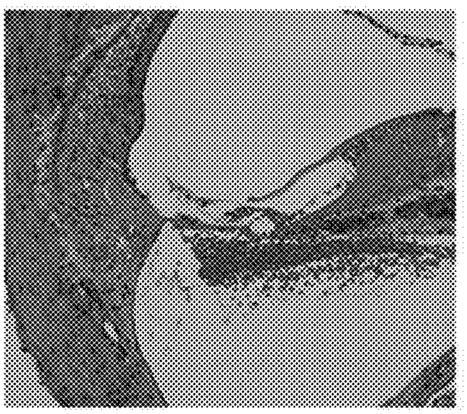

FIGS. 21B and 21D are images of the inner sections of FIGS. 21A and 21C respectively after application of liposomal formulation TF-RnB for one month.

Figure 22A:
FIGS. 22A, 22B, 22C and 22D correspond to an image sequence for a tympanic membrane exposed to a liposomal formulation of RnB dye showing that RnB dye is present in the middle ear.
Figure 22C:
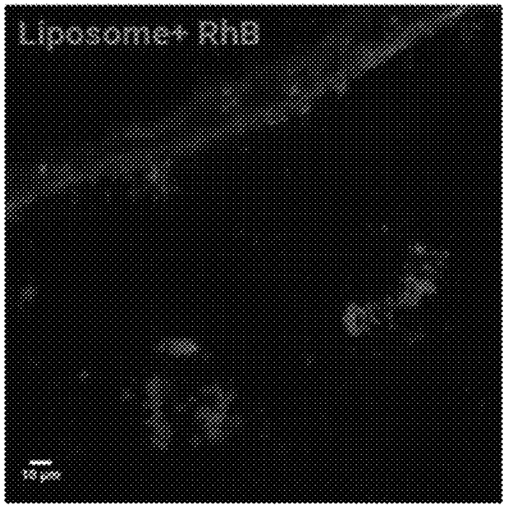
Figure 22B:
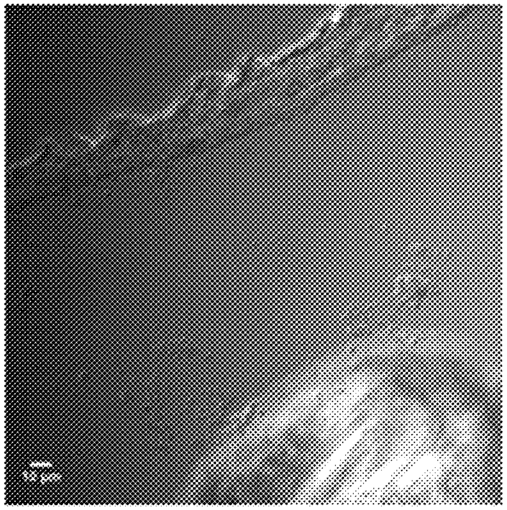
Figure 22D:
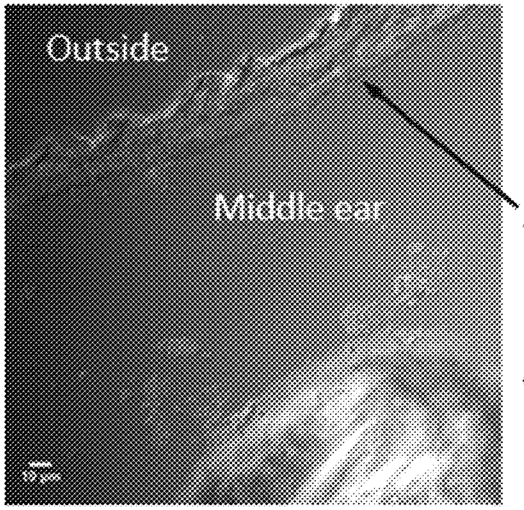

FIGS. 22A, 22B, 22C and 22D correspond to an image sequence for a tympanic membrane exposed to a liposomal formulation of RnB dye showing that RnB dye is present in the middle ear. FIG. 22A is showing imaging specificity of DAPI in blue. FIG. 22C is showing imaging specificity to TF-RhB in red. FIG. 22B is a differential interference contrast (DIC) image. FIG. 22D is showing a color composite overlay of the images in FIGS. 12A, 12B, and 12C.

Figures 23A, 23B, 23C, 23D, 23E:
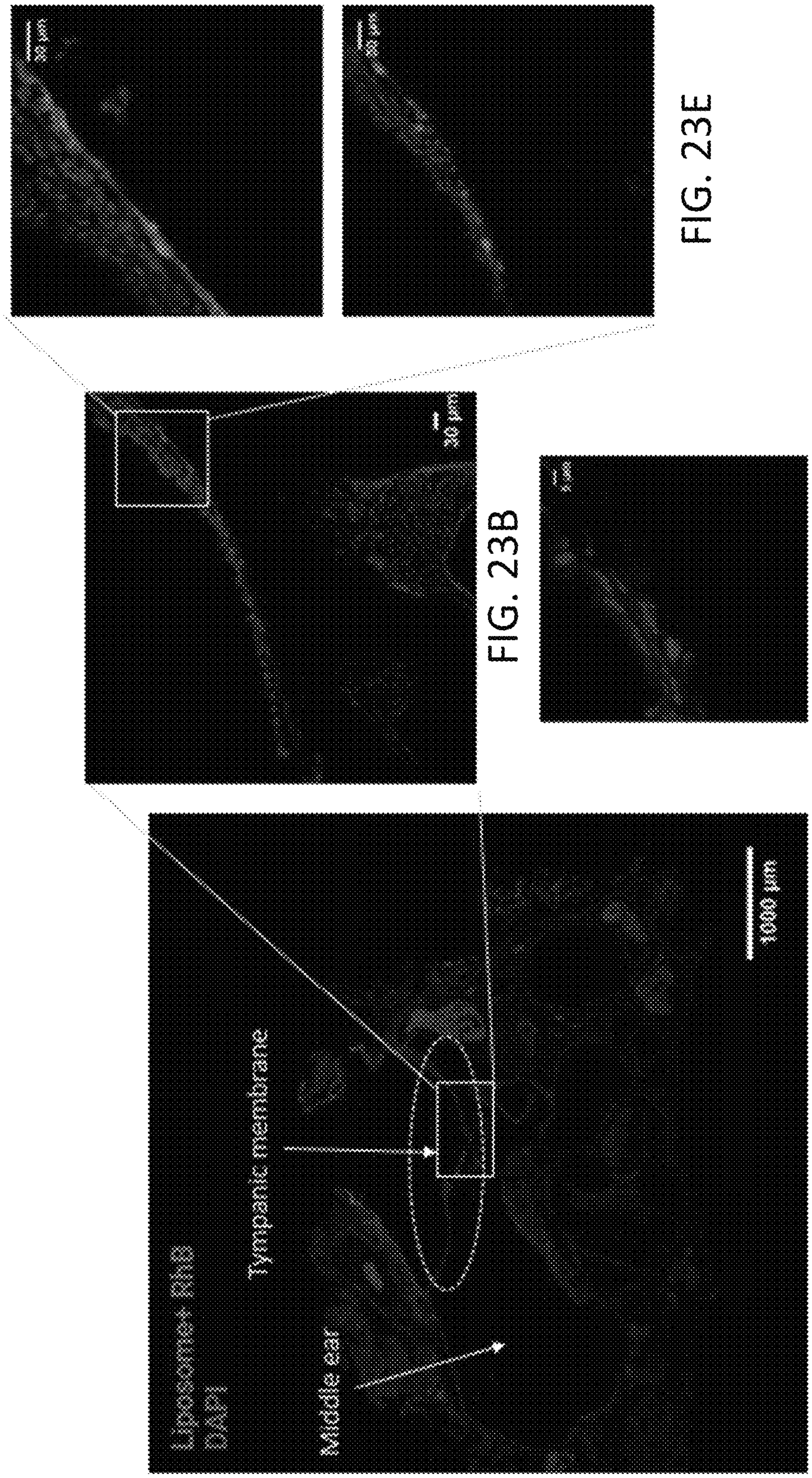
FIG. 23A is an image of an inner ear section including the tympanic membrane and middle ear after 6 hours exposure to a liposomal formulation B1. The image shows the presence of the liposomal formulation B1 labeled with Rhodamine B (liposome+RhB) in red and DAPI in blue.
FIGS. 23B and 23C are enlargements of the indicated portion within the white square of the tympanic membrane of FIG. 23A showing the presence of the RhB passing through the tympanic membrane.
FIGS. 23D and 23E are further enlargements of the indicated portion within the white square of the tympanic membrane in FIG. 23B and the presence of RhB.

FIG. 23A is an image of an inner ear section including the tympanic membrane and middle ear after 6 hours exposure to a liposomal formulation B1. The image shows the presence of the liposomal formulation B1 labeled with Rhodamine B (liposome+RhB) in red and DAPI in blue.

FIGS. 23B and 23C are enlargements of the indicated portion within the white square of the tympanic membrane of FIG. 23A showing the presence of the RhB passing through the tympanic membrane.

FIGS. 23D and 23E are further enlargements of the indicated portion within the white square of the tympanic membrane in FIG. 23B and the presence of RhB.

Figures 24A, 24B, 24C:
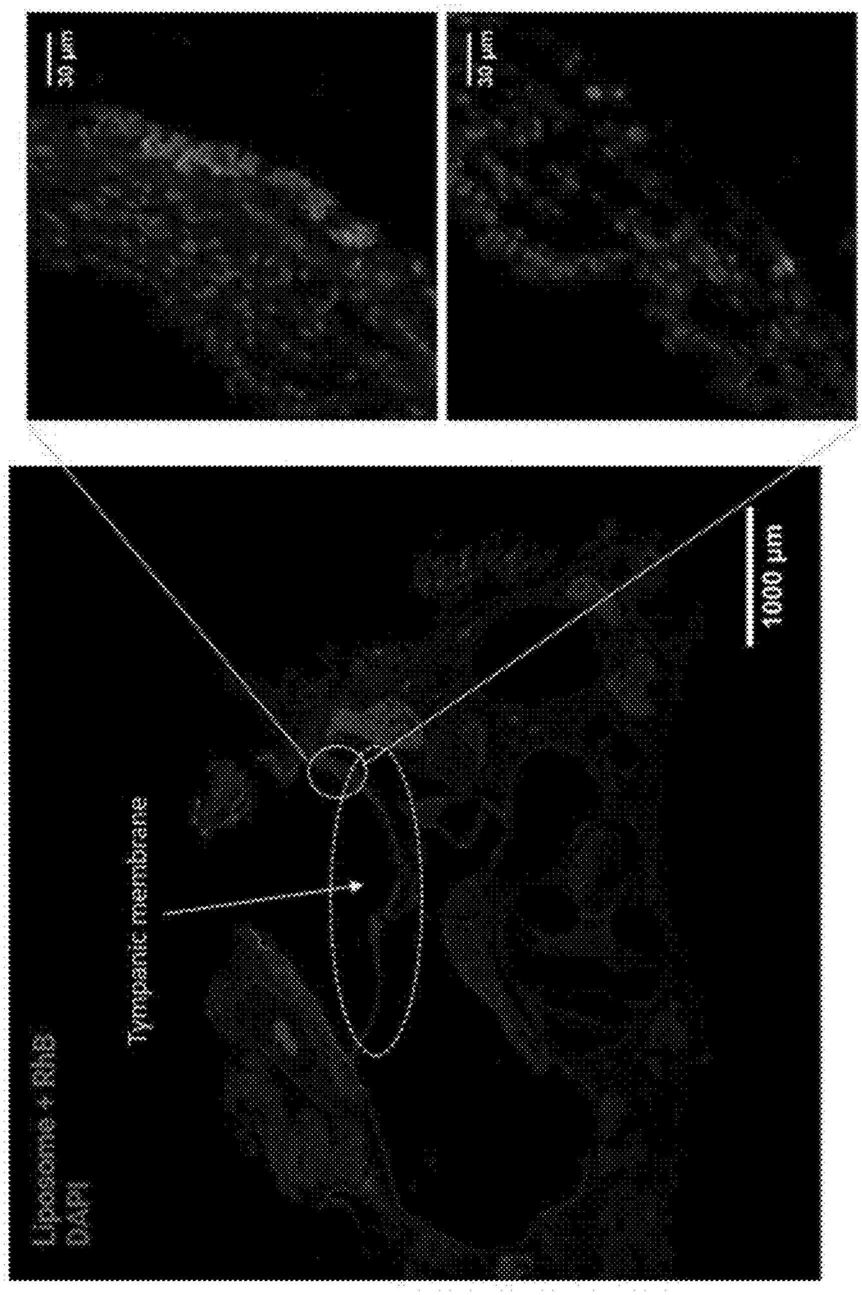
FIG. 24A is an image of an inner ear section including the tympanic membrane (dashed yellow oval) and middle ear after 6 hours exposure to a liposomal formulation B1. The image shows the presence of the liposomal formulation B1 labeled with Rhodamine B (liposome+RhB) in red and DAPI in blue.
FIGS. 24B and 24C are enlargements of the indicated portion within the white circle of the tympanic membrane of FIG. 24A showing the presence of the RhB passing through the tympanic membrane.

FIG. 24A is an image of an inner ear section including the tympanic membrane (dashed yellow oval) and middle ear after 6 hours exposure to a liposomal formulation B1. The image shows the presence of the liposomal formulation B1 labeled with Rhodamine B (liposome+RhB) in red and DAPI in blue.

FIGS. 24B and 24C are enlargements of the indicated portion within the white circle of the tympanic membrane of FIG. 24A showing the presence of the RhB passing through the tympanic membrane.

Figure 25C:
FIG. 25C is a further enlargement of the indicated portion within the white rectangle of the tympanic membrane of FIG. 25B showing the presence of the RhB in red.
Figure 25B:
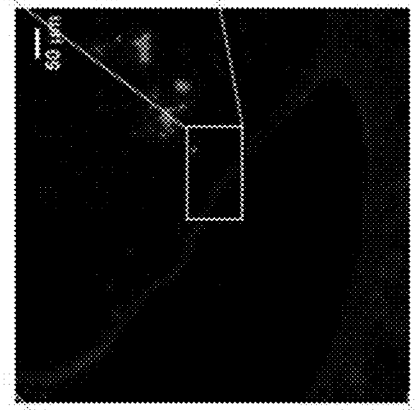
FIG. 25B is an enlargement of the indicated portion within the white rectangle of the tympanic membrane of FIG. 25A showing the presence of the RhB passing through the tympanic membrane.
Figure 25A:
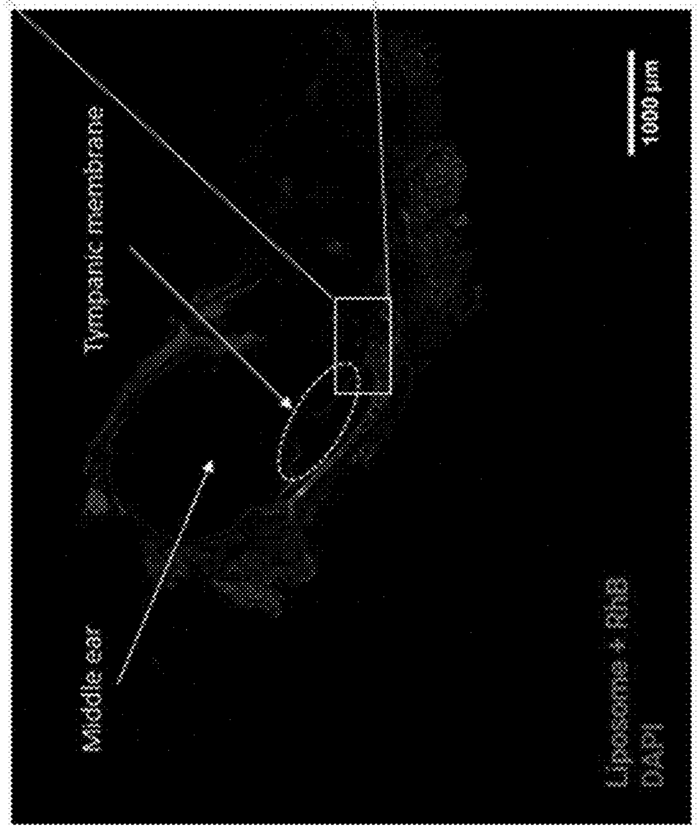
FIG. 25A is an image of an inner ear section including the tympanic membrane (dashed yellow oval) and middle ear after 24 hours exposure to a liposomal formulation B1. The image shows the presence of the liposomal formulation B1 labeled with Rhodamine B (liposome+RhB) in red and DAPI in blue.

FIG. 25A is an image of an inner ear section including the tympanic membrane (dashed yellow oval) and middle ear after 24 hours exposure to a liposomal formulation B1. The image shows the presence of the liposomal formulation B1 labeled with Rhodamine B (liposome+RhB) in red and DAPI in blue.

FIG. 25B is an enlargement of the indicated portion within the white rectangle of the tympanic membrane of FIG. 25A showing the presence of the RhB passing through the tympanic membrane.

FIG. 25C is a further enlargement of the indicated portion within the white rectangle of the tympanic membrane of FIG. 25B showing the presence of the RhB in red.

Figures 26A, 26B, 26C, 26D:
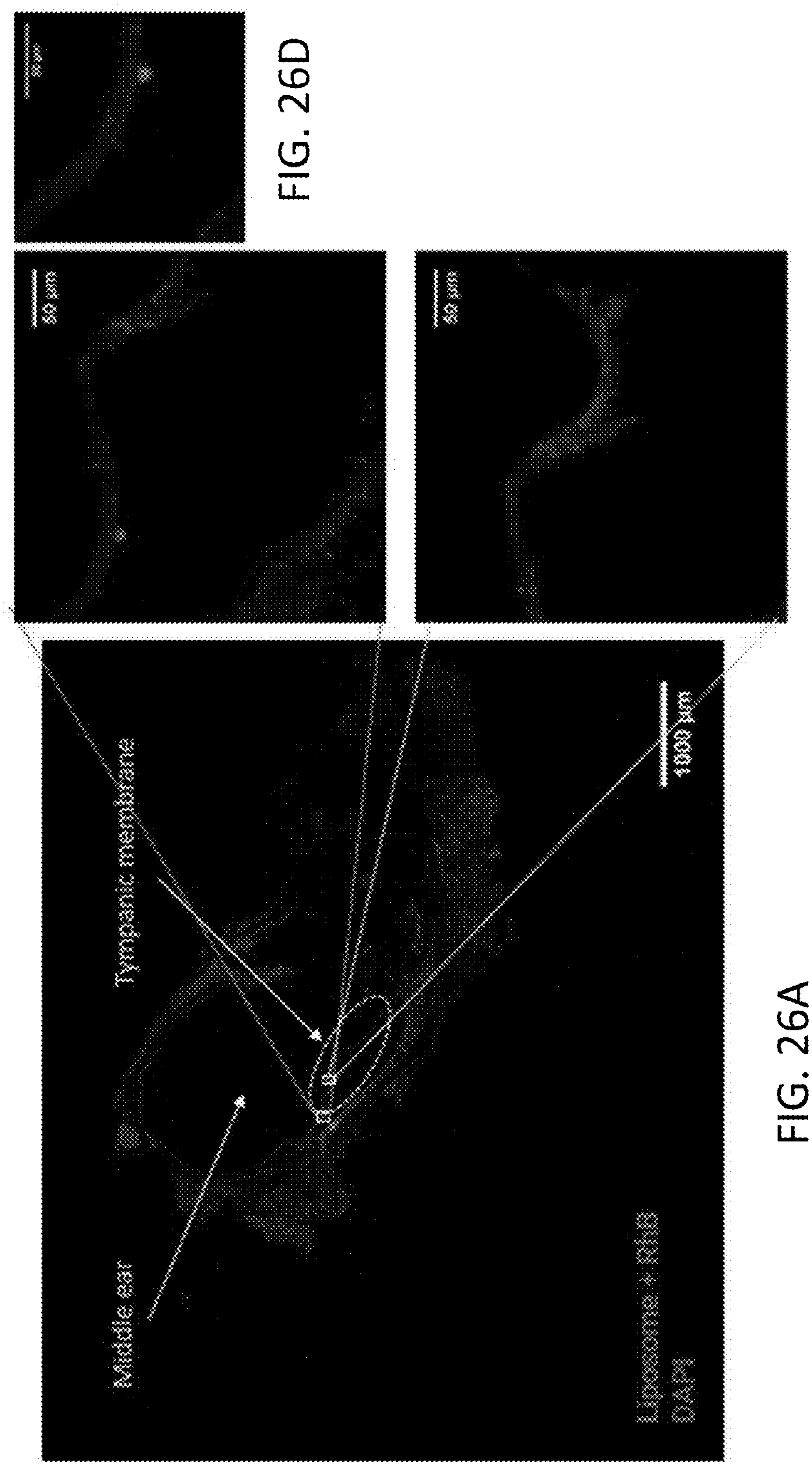
FIG. 26A is an image of an inner ear section including the tympanic membrane (dashed yellow oval) and middle ear after 24 hours exposure to a liposomal formulation B1. The image shows the presence of the liposomal formulation B1 labeled with Rhodamine B (liposome+RhB) in red and DAPI in blue.
FIG. 26B is an enlargement of a portion of the tympanic membrane in the left most white square of the tympanic membrane of FIG. 26A showing the presence of the RhB in red.
FIG. 26C is an enlargement of a portion of the tympanic membrane in the right most white square of the tympanic membrane of FIG. 26A showing the presence of the RhB in red.
FIG. 26D is a further enlargement of the indicated portion of the tympanic membrane in FIG. 26B showing the presence of RhB in red.

FIG. 26A is an image of an inner ear section including the tympanic membrane (dashed yellow oval) and middle ear after 24 hours exposure to a liposomal formulation B1. The image shows the presence of the liposomal formulation B1 labeled with Rhodamine B (liposome+RhB) in red and DAPI in blue.

FIG. 26B is an enlargement of a portion of the tympanic membrane in the left most white square of the tympanic membrane of FIG. 26A showing the presence of the RhB in red.

FIG. 26C is an enlargement of a portion of the tympanic membrane in the right most white square of the tympanic membrane of FIG. 26A showing the presence of the RhB in red.

FIG. 26D is a further enlargement of the indicated portion of the tympanic membrane in FIG. 26B showing the presence of RhB in red.

Figure 1:
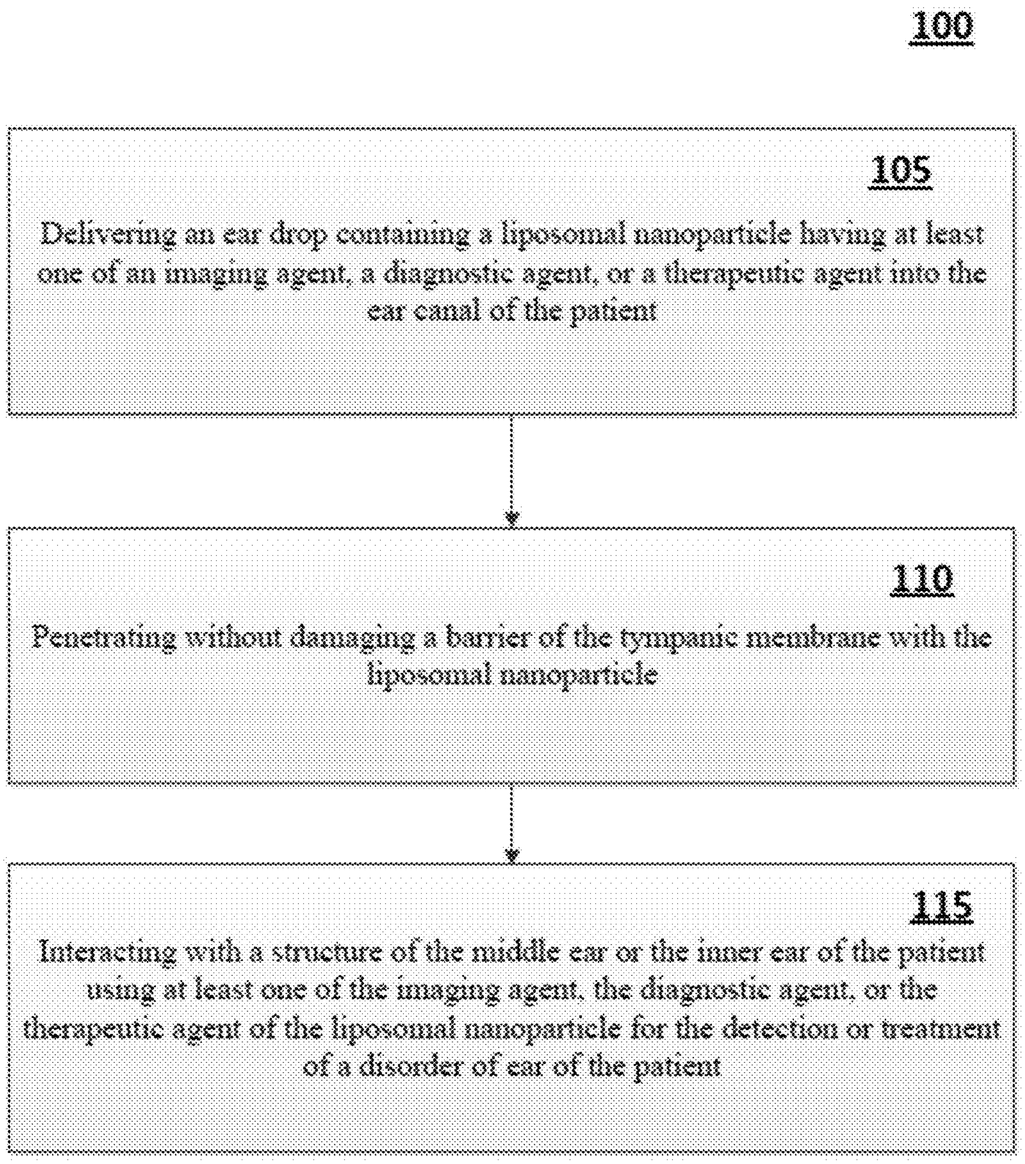
FIG. 1 is a flow chart of an example method of treatment of an ear disorder.
Figure 4:
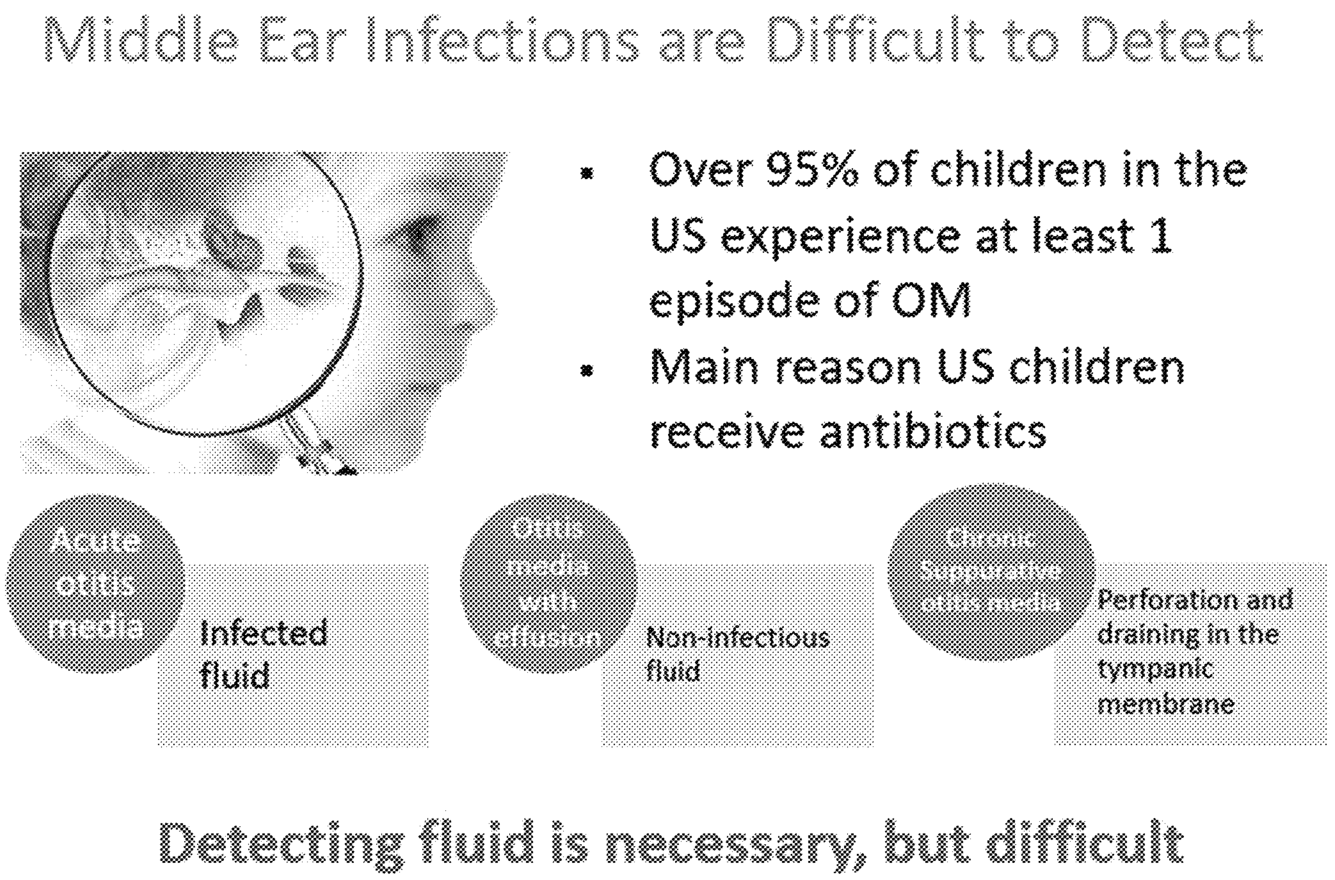
FIG. 4 is an infographic summarizing various degrees of middle ear disorders.

Embodiments of the above may be employed in a wide variety of methods of detecting or treating a disorder in an ear of a patient. For example, in the exemplary method 100 in FIG. 1, there may be a first step 105 of delivering an ear drop containing a liposomal nanoparticle having at least one of an imaging agent, a diagnostic agent, or a therapeutic agent into the ear canal of the patient. Next, as a result of the advantageous formulation of the ear drop embodiment, the liposomal formulation is penetrating without damaging a barrier of the TM and RWM with the liposomal nanoparticle (step 110). Thereafter, with the liposomal cargo safely within the structures of the inner and middle ear, there is a step 115 of interacting with a structure of the middle ear or the inner ear of the patient using at least one of the imaging agent, the diagnostic agent, or the therapeutic agent of the liposomal nanoparticle for the detection or treatment of a disorder of ear of the patient.

In still other aspects or alternatives, the liposomal nanoparticle is adapted for detection of inflammatory fluid in the middle ear and an indication of infection in the detected fluids as part of a diagnosis of otitis media. In still other aspects, the imaging agent comprises an inflammation targeted probe that fluoresce comprising a step of detecting through the tympanic layer a presence of a bacterial fluid and an indication of whether the fluid is infected based on the response of the targeted probe that can fluoresce within the visible, NIR and short-wave infrared spectrum.

In other alternatives the liposomes can deliver mucolytic medications to the middle ear to decrease the viscosity of the middle ear fluid. Additionally or optionally, in some embodiments the nanoparticles may deliver mucolytic drugs to the middle ear fluid, which can soften the fluid (e.g., reduce its viscosity and stickiness) thereby facilitating its discharge from the nose of the patient.

In still other alternative embodiments, formulations of the inventive nanoparticle may be adapted for combination therapy to enhance the efficacy of the treatment, or still further as a multi-modal solution that can be used for imaging and therapy enabled by the delivery of a single product into the ear canal.

In still further alternatives, an embodiment of the nanoparticles may deliver antibiotics or combinations of antibiotics and other anti-microbial drugs to eradicate bacterial infection in the middle ear. In still further embodiments, there is provided a formulation of the nanoparticle adapted for treatment, removal or elimination of bacteria based or other undesired biofilms in the middle ear. Additionally, or optionally, the nanoparticle formulation may be formulated to specifically target those bacteria or biofilms that are hard to penetrate or treat with antibiotics. In still further alternatives, the liposomal nanoparticle comprises lipids adapted for penetration of biofilms within the ear.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of detecting or treating a disorder in a middle ear or an inner ear of a patient, comprising:

delivering an ear drop containing a nanoparticle having an imaging agent, and one or both of a diagnostic agent and a therapeutic agent into the ear canal of the patient, the imaging agent configured to fluoresce in one of a visible, NIR and short-wave infrared spectrum;

penetrating without damaging the tympanic membrane or round window with the nanoparticle;

delivering the agent or agents to the middle ear or the inner ear of the patient for the detection or treatment of a disorder of the ear of the patient; and detecting fluorescence of the imaging agent to detect a presence of the nanoparticle within the middle ear or the inner ear.

2. The method of claim 1, wherein multiple imaging agents, diagnostic agents, or therapeutic agents are delivered by the same nanoparticle.

3. The method of claim 1 wherein the nanoparticle is adapted for detection or treatment of otitis media.

4. The method of claim 1 wherein the nanoparticle is adapted for detection or changing properties of fluid as part of a diagnosis or treatment of otitis media with effusion.

5. The method of claim 1 wherein the nanoparticle is adapted for detection or eradication of infection in fluid as part of a diagnosis or treatment of acute or chronic otitis media.

6. The method of claim 1 wherein the imaging agent comprises an inflammation targeted probe that will fluoresce, the method further comprising detecting one or both of a presence of a fluid within the middle ear or the inner ear and an indication of whether the fluid is infected.

7. The method of claim 6 wherein the probe will fluoresce within the visible, NIR and short-wave infrared spectrum.

8. The method of claim 1 wherein the nanoparticle is a lipid-based or liposomal formulation.

9. The method of claim 1, wherein the nanoparticle comprises a vesicular structure composed of lipids arranged in a bilayer formulated for trans-tympanic membrane delivery, and wherein the imaging agent, and the one or both of a diagnostic agent and a therapeutic agent are loaded onto the structure.

10. The method of claim 9, wherein the lipids comprise phospholipids.

11. The method of claim 9, wherein the lipids comprise a hydrophilic surface and core and a hydrophobic interior of the bilayer.

12. The method of claim 9, wherein the at least one of the imaging agent, the diagnostic agent or the therapeutic agent are loaded on, in or within a portion of a hydrophilic surface, a hydrophilic core, or interior or combinations thereof.

13. The method of claim 1, wherein the ear drop is delivered to deliver mucolytic or anti-microbial drugs to the middle ear.

14. The method of claim 1, wherein the ear drop is delivered to deliver therapeutic or protective agents to the inner ear.

15. The method of claim 1, wherein the nanoparticle comprises a formulation comprising multiple compounds loaded simultaneously on, in or within the nanoparticle.

16. A method of detecting or treating a disorder in a middle ear or an inner ear of a patient, comprising:

delivering an ear drop containing a nanoparticle comprising an imaging agent, and one or both of a diagnostic agent and a therapeutic agent into the ear canal of the patient, the imaging agent configured to fluoresce in one of a visible, NIR and short-wave infrared spectrum, the nanoparticle penetrating without damaging the tympanic membrane and enter the middle ear; and detecting fluorescence of the imaging agent to detect a presence of the nanoparticle within the middle ear or the inner ear.

17. The method of claim 16, further comprising detecting through the tympanic layer a presence of a fluid and an indication of whether the fluid is infected based on the fluorescence of the imaging agent.

18. The method of claim 16, wherein the imaging agent comprises one or both of a hydrophobic imaging agent and a hydrophilic imaging agent.

19. A method of detecting or treating a disorder in a middle ear or an inner ear of a patient, comprising:

delivering an ear drop containing a nanoparticle comprising an imaging agent, and one or both of a diagnostic agent and a therapeutic agent into the ear canal of the patient, the imaging agent configured to fluoresce in one of a visible, NIR and short-wave infrared spectrum, the nanoparticle penetrating without damaging the tympanic membrane and enter the middle ear; and detecting through the tympanic layer a presence of a fluid and an indication of whether the fluid is infected based on the fluorescence of the imaging agent.

* * * * *